United States Patent
Cooke et al.

(10) Patent No.: US 8,043,228 B2
(45) Date of Patent: *Oct. 25, 2011

(54) MEDICAL INSTRUMENT

(75) Inventors: David Cooke, Harvard, MA (US);
Michael John Bettuchi, Middletown, CT (US); Leland Ray Adams, Ansonia, CT (US); Frederick Timothy Karl, Newtown, CT (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/498,206

(22) Filed: Jul. 6, 2009

(65) Prior Publication Data
US 2009/0270761 A1 Oct. 29, 2009

Related U.S. Application Data

(63) Continuation of application No. 11/392,088, filed on Mar. 29, 2006, now abandoned, which is a continuation of application No. 10/300,249, filed on Nov. 20, 2002, now Pat. No. 7,022,085.

(51) Int. Cl.
*A61B 10/00* (2006.01)
(52) U.S. Cl. ..................................... 600/564
(58) Field of Classification Search .......... 600/562–568; 606/167, 170; 604/159, 239, 264, 272, 506, 604/512
See application file for complete search history.

(56) References Cited

U.S. PATENT DOCUMENTS

| | | |
|---|---|---|
| 4,274,414 A | 6/1981 | Johnson et al. |
| 4,844,064 A | 7/1989 | Thimsen et al. |
| 4,924,878 A | 5/1990 | Nottke |
| 4,953,558 A | 9/1990 | Akerfeldt |
| 4,958,625 A | 9/1990 | Bates et al. |
| 5,195,533 A | 3/1993 | Chin et al. |
| 5,368,045 A | 11/1994 | Clement et al. |
| 5,476,101 A | 12/1995 | Schramm et al. |
| 5,507,298 A | 4/1996 | Schramm et al. |
| 5,660,186 A | 8/1997 | Bachir |
| 5,685,852 A | 11/1997 | Turkel et al. |
| 5,718,237 A | 2/1998 | Haaga |
| 5,779,647 A | 7/1998 | Chau et al. |
| 5,842,999 A | 12/1998 | Pruitt et al. |
| 5,989,196 A | 11/1999 | Chu et al. |

(Continued)

FOREIGN PATENT DOCUMENTS

DE 100 34 297 4/2001

(Continued)

OTHER PUBLICATIONS

The International Search Report issued on Apr. 27, 2004 by the International Searching Authority: European Patent Office—The Netherlands, in PCT application No. PCT/US03/07597, filed Nov. 20, 2003.

*Primary Examiner* — Brian Szmal
(74) *Attorney, Agent, or Firm* — Fish & Richardson P.C.

(57) ABSTRACT

A method includes actuating a lever to move a cannula of a medical instrument from a first extended position to second retracted position; and actuating the lever to move a stylet of the medical instrument from a third extended position to a fourth retracted position. Actuating the lever comprises moving the lever from a first lever position spaced apart from a housing of the medical instrument to a second lever position closer to the housing.

19 Claims, 10 Drawing Sheets

U.S. PATENT DOCUMENTS

| | | | |
|---|---|---|---|
| 5,993,399 | A | 11/1999 | Pruitt et al. |
| 6,015,391 | A | 1/2000 | Rishton et al. |
| 6,033,411 | A | 3/2000 | Preissman |
| 6,050,955 | A | 4/2000 | Bryan et al. |
| 6,086,543 | A | 7/2000 | Anderson et al. |
| 6,126,617 | A | 10/2000 | Weilandt et al. |
| 6,142,955 | A | 11/2000 | Farascioni et al. |
| 6,165,136 | A | 12/2000 | Nishtala |
| 6,221,030 | B1 | 4/2001 | Avaltroni |
| 6,293,957 | B1 | 9/2001 | Peters et al. |
| 6,358,217 | B1 | 3/2002 | Bourassa |
| 6,402,701 | B1 | 6/2002 | Kaplan et al. |
| 6,428,486 | B2 | 8/2002 | Ritchart et al. |
| 6,488,636 | B2 | 12/2002 | Bryan et al. |
| 6,497,706 | B1 | 12/2002 | Burbank et al. |
| 6,544,192 | B2 | 4/2003 | Bryan et al. |
| 6,620,111 | B2 | 9/2003 | Stephens et al. |
| 6,730,045 | B2 | 5/2004 | Finer |
| 6,849,080 | B2 | 2/2005 | Lee et al. |
| 7,008,382 | B2 | 3/2006 | Adams et al. |
| 7,022,085 | B2 | 4/2006 | Cooke et al. |
| 7,201,722 | B2 | 4/2007 | Krueger |

FOREIGN PATENT DOCUMENTS

| | | |
|---|---|---|
| EP | 0 536 888 | 4/1993 |
| JP | 1-198537 | 8/1989 |
| JP | 4-509758 | 11/1992 |
| JP | 6-197898 | 6/1994 |
| JP | 10-179592 | 7/1998 |
| JP | 2000-506044 | 5/2000 |
| JP | 2002-000609 | 1/2002 |
| JP | 2002-514458 | 5/2002 |

MEDICAL INSTRUMENT

CROSS-REFERENCE TO RELATED APPLICATIONS

This application is a continuation of and claims the benefit of priority under 35 U.S.C. §120 to U.S. application Ser. No. 11/392,088, filed Mar. 29, 2006, which is a continuation of U.S. application Ser. No. 10/300,249, filed Nov. 20, 2002, the entire contents of both of which are being hereby fully incorporated by reference.

TECHNICAL FIELD

The invention relates to medical instruments.

BACKGROUND

A biopsy needle instrument can be used to obtain a tissue specimen for microscopic examination, e.g., to determine malignancy, while preferably subjecting the patient to the least trauma. In some embodiments, the instrument has of a long, thin probe, called a stylet, within a close-fitting hollow needle, called a cannula. The stylet has a notch into which tissue can prolapse when the stylet enters the tissue.

During use, a firing device first projects the stylet into tissue, followed immediately by the cannula. As the cannula slides over the stylet, the cannula severs from the surrounding mass tissue that has prolapsed into the notch of the stylet, and captures the prolapsed tissue as a specimen within the notch. The instrument can then be withdrawn and the piece of tissue removed from the stylet.

SUMMARY

The invention relates to medical instruments.

In one aspect, the invention features a medical instrument including a housing, a stylet, a cannula, and a lever. The stylet has a portion in the housing and is movable between an extended position and a retracted position. The cannula coaxially receives the stylet and has a portion in the housing. The cannula is movable between an extended position and a retracted position. The lever is coupled, for example, pivotally, to the housing. The lever is configured to move, for example, sequentially, the stylet from the extended position to the retracted position, and to move the cannula from the extended position to the retracted position.

Embodiments may include one or more of the following features. The engaging element engages with the housing when the cannula is in the retracted position. The instrument further includes a linkage attached to the lever, the linkage being engageable with the cannula block to move the cannula to the retracted position. The instrument further includes a stylet block attached to a proximal end of the stylet, and a latch in the housing, the latch and the stylet block engaging when the stylet is in the retracted position. The instrument further includes a linkage attached to the lever, the linkage being engageable with the stylet block to move the stylet to the retracted position. The instrument further includes a first trigger engageable with the latch to release the stylet from the retracted position. The first trigger pivotally moves the latch to disengage the latch from the stylet block. The instrument further includes a second trigger engageable with the latch to release the stylet from the retracted position.

The instrument can further include a cannula block attached to a proximal end of the cannula, the cannula block having an engaging element capable of releasably holding the cannula in the retracted position.

The instrument can further include a stylet block attached to a proximal end of the stylet, a cannula block attached to a proximal end of the cannula, and a linkage attached to the lever, the linkage capable of being in a first position in which the linkage is engageable with the cannula block to move the cannula to the retracted position without moving the stylet block, and in a second position in which the linkage is engageable with the stylet block to move the stylet to the retracted position.

Embodiments may include one or more of the following features. The instrument further includes a first trigger configured to release the stylet from the retracted position. The first trigger is located at a proximal end of the housing. The first trigger and the lever are located on opposing surfaces of the housing. The instrument further includes a second trigger configured to release the stylet from the retracted position. The instrument further includes a lock engageable with the lever when the stylet block is in the retracted position. The instrument further includes an indicator capable of being in a condition representative of when the stylet is in the second retracted position.

The instrument can further include a first trigger configured to hold the stylet in the retracted position, and a second trigger engageable with the first trigger, wherein the first and second triggers are configured to release the stylet from the retracted position. The first trigger can be pivotally attached to the housing. In some embodiments, the first trigger has a proximal end, and the second trigger has a distal end configured to engage with the proximal end of the first trigger. The proximal and distal ends can be angled.

In another aspect, the invention features a medical instrument including a housing, a stylet, a cannula, a lever, and a linkage. The\a stylet has a portion in the housing and is movable between an extended position and a retracted position. The cannula coaxially receives the stylet and has a portion in the housing. The cannula is movable between an extended position and a retracted position. The lever is pivotally coupled to the housing. The linkage is attached to the lever. The linkage is capable of being in a first position in which the linkage is capable of moving the cannula to the retracted position without moving the stylet, and in a second position in which the linkage is capable of moving the stylet to the retracted position. The instrument can further include two triggers configured to release the stylet from the retracted position.

In another aspect, the invention features a medical instrument including a housing, a stylet attached to the housing, the stylet being movable between an extended position and a retracted position, and an indicator associated with the housing, the indicator providing a visual indication of the position the stylet by a change in color.

In another aspect, the invention features a medical instrument including a housing, a stylet attached to the housing, the stylet being movable between an extended position and a retracted position, and an indicator associated with the housing, the indicator providing a visual indication of the position the stylet by a change in symbol.

In another aspect, the invention features a method including actuating a lever to move a stylet from a first extended position to a second retracted position, and actuating the lever to move a cannula from a third extended position to a fourth retracted position.

Embodiments may include one or more of the following features. The method further includes releasing the lever after the stylet is moved to the second retracted position. The method further includes locking the lever after the cannula is moved. The method further includes sliding a trigger to release the stylet from the second retracted position. The method further includes pushing a trigger to release the stylet from the second retracted position. The stylet is moved without moving the cannula. The method further includes pushing a first trigger or a second trigger to release the stylet from the retracted position. Pushing the second trigger can move the first trigger out of engagement with the stylet.

In another aspect, the invention features a method including pivotally actuating a lever to move a stylet from an extended position to a retracted position.

In another aspect, the invention features a method including pivotally actuating a lever to move a cannula from an extended position to a retracted position.

In another aspect, the invention features a medical instrument including a housing, a stylet attached to the housing, the stylet being movable between an extended position and a retracted position, and two triggers associated with the housing, wherein the triggers are capable of releasing the stylet from the retracted position.

One of the triggers can be at a proximal end of the housing. One of the triggers can be slidably associated with the housing.

In another aspect, the invention features a medical instrument including a housing, a stylet having a portion in the housing, the stylet being movable between an extended position and a retracted position, a cannula coaxially receiving the stylet and having a portion in the housing, the cannula being movable between an extended position and a retracted position, and a member coupled to the housing, the member being capable of moving the stylet from the extended position to the retracted position, and when separately engaged, moving the cannula from the extended position to the retracted position. The member can include a lever. The member can be engaged by a user's hand, e.g., palm and/or fingers. Embodiments of the aspect of the invention may include one or more of the features described above and below, in any combination.

Embodiments may have one or more of the following advantages. The instrument can be relatively easy to load prior to firing the instrument. The lever of the instrument provides good mechanical advantage and is used to load the stylet and the cannula with the same motion. The instrument includes two trigger mechanisms, which enhances the versatility and convenience of the instrument. For example, depending on a target site and/or preference of a user, a radiologist can prefer to use a side trigger, while a urologist can prefer the rear trigger.

Other aspects, features, and advantages of the invention will be apparent from the description of the preferred embodiments thereof and from the claims.

DETAILED DESCRIPTION

Figure 1:
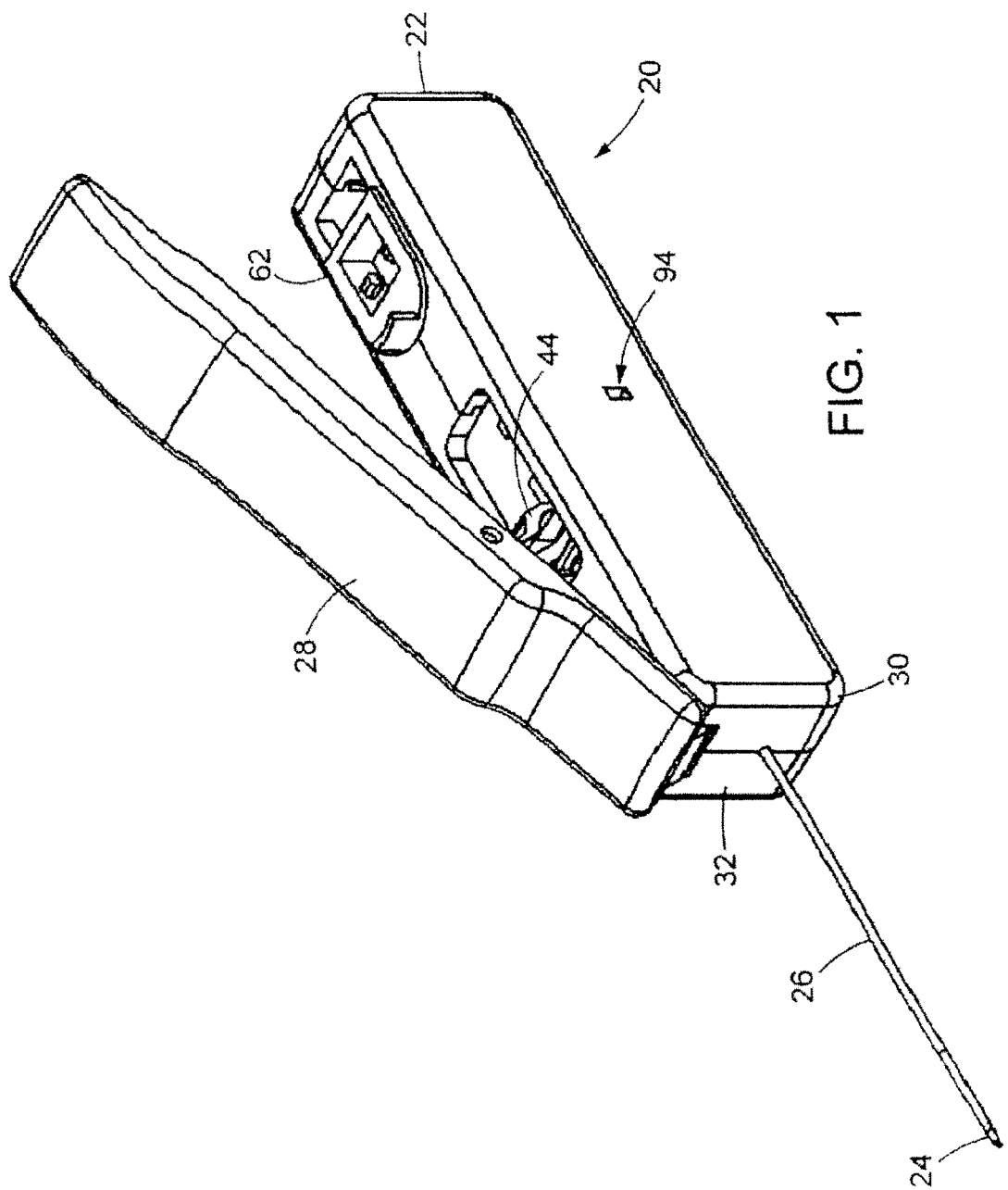
FIG. 1 is a perspective view of an embodiment of a biopsy instrument.
Figure 2A:
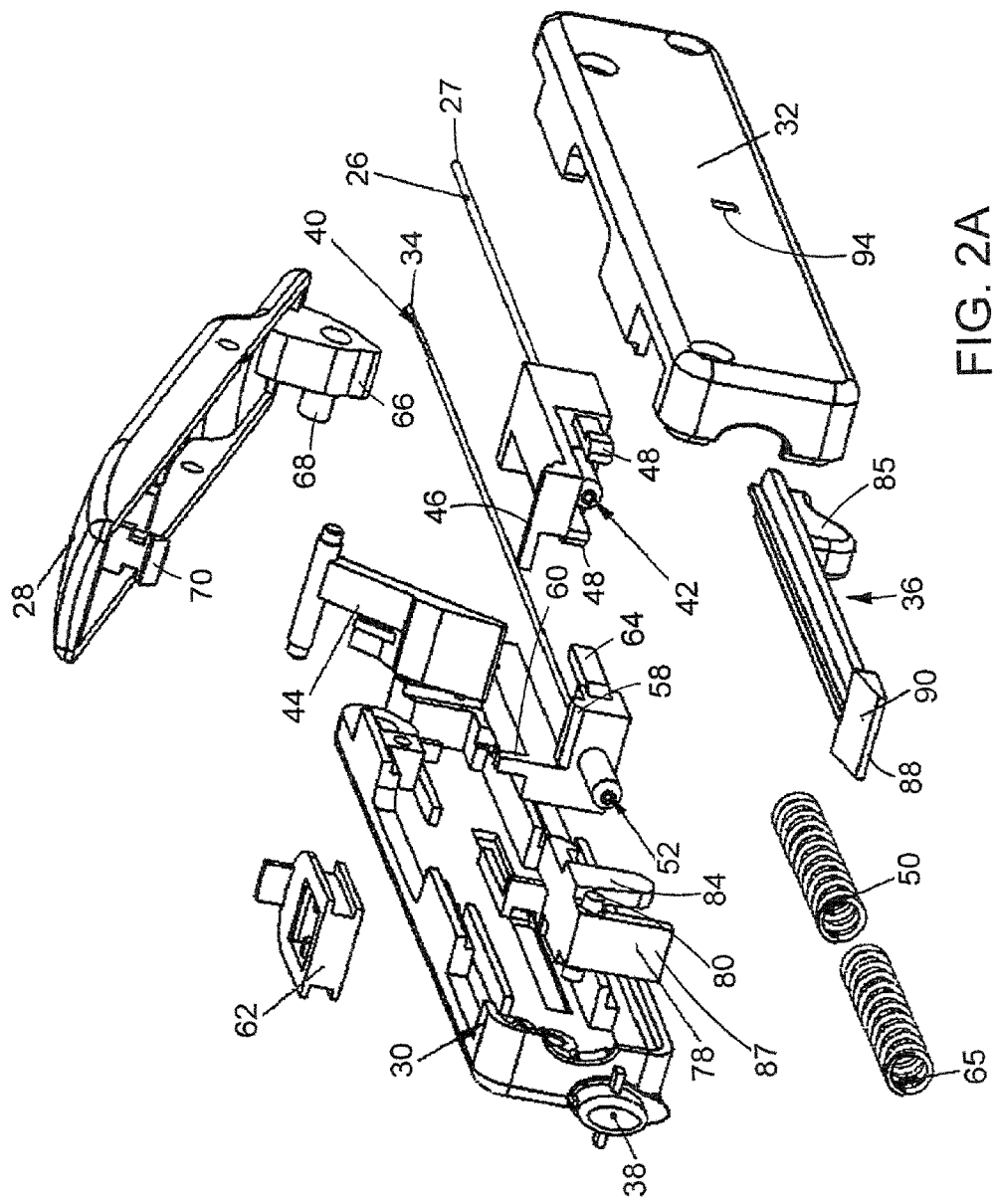
FIGS. 2A and 2B are exploded, perspective views of the biopsy instrument of FIG. 1, at different angles.
Figure 2B:
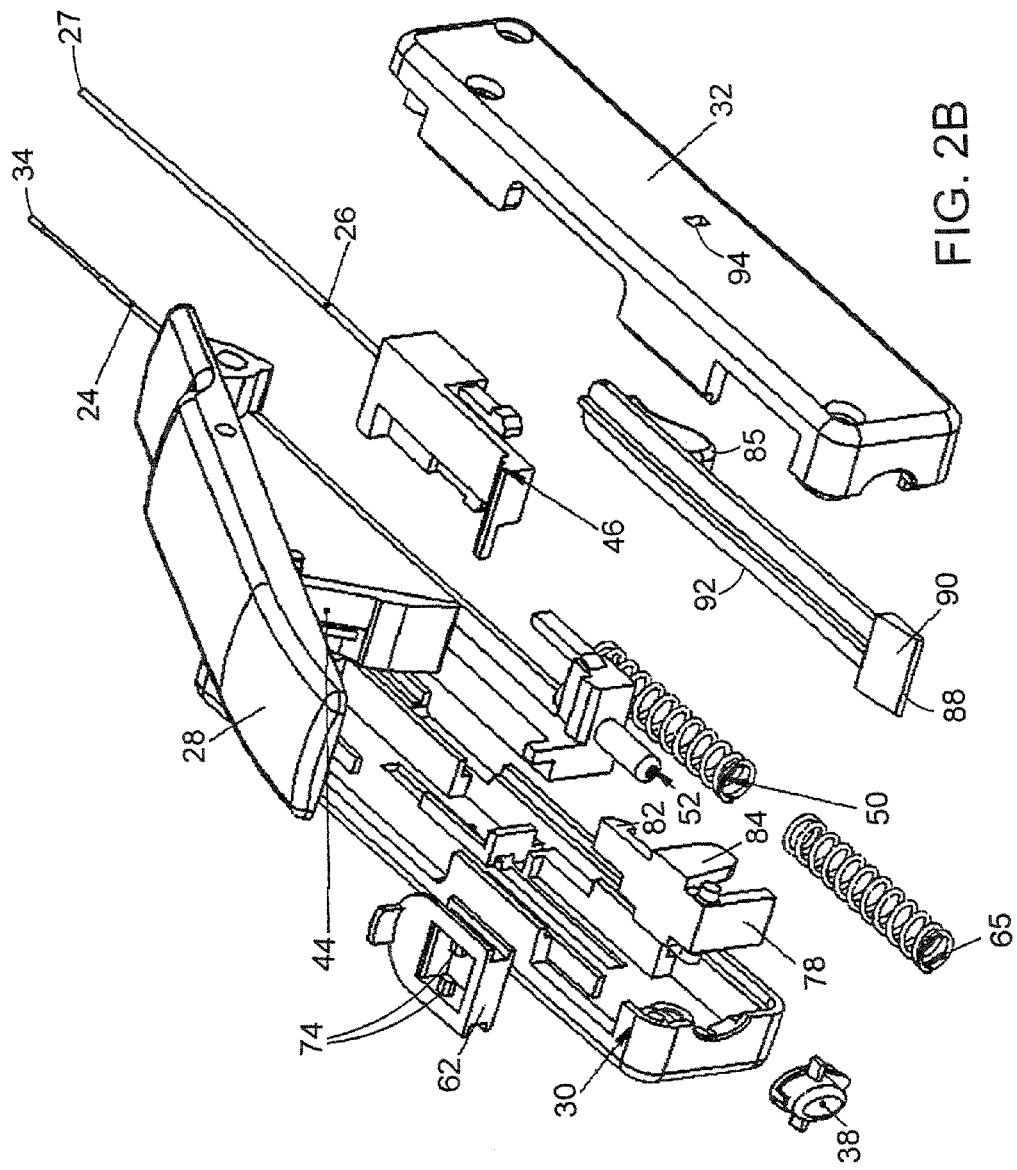
Figure 3A:
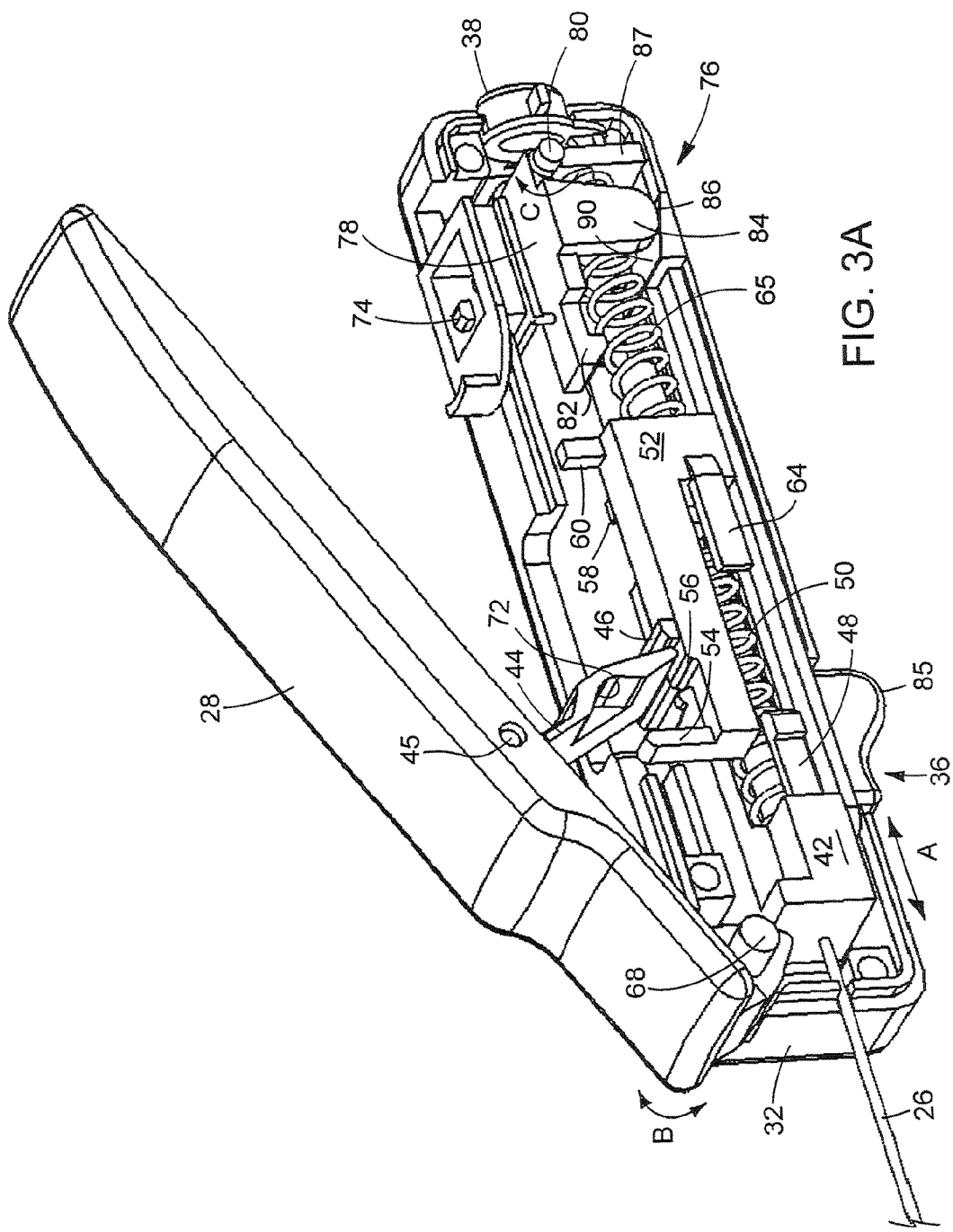
FIGS. 3A, 3B, 3C, 3D, and 3E illustrate the biopsy instrument of FIG. 1 at various stages of operation.

Referring to FIGS. 1, 2A, 2B, and 3A, a biopsy instrument 20 includes a housing 22, a stylet 24, a cannula 26, a lever 28 pivotally attached to the housing, a side trigger 36, and a rear trigger 38. Housing 22 includes a left shell 30 and a right shell 32 (as shown in Figures) that are bonded together. Stylet 24 and cannula 26 have portions located within housing 22 and are configured to be axially movable relatively to each other, between retracted positions and extended positions. As shown in FIG. 3A, stylet 24 and cannula 26 are in their extended positions. During use, stylet 24 and cannula 26 are loaded or cocked to their retracted positions, ready to be triggered. When stylet 24 and cannula 26 are triggered, they rapidly move distally to their extended positions, e.g., to collect a tissue specimen that has prolapsed into a notch 40 of the stylet. Lever 28 is connected to a linkage 44 configured to move stylet 24 and cannula 26 from their extended positions to their retracted or loaded positions. In particular, lever 28 is part of a mechanism that is used to load both stylet 24 and cannula 26 to their retracted positions. After stylet 24 and cannula 26 are loaded, either side trigger 36 or rear trigger 38 can be used to release the stylet and the cannula to their extended positions.

Referring to FIGS. 2A, 2B, and 3A, cannula 26 is generally a hollow sheath, e.g., made of stainless steel, that receives stylet 24. At its distal end 27, cannula 26 is configured to sever tissue that has prolapsed into notch 40. From distal end 27, cannula 26 extends into housing 22 where the cannula is attached to an axially movable (arrow A) cannula block 42. Cannula block 42 includes a raised portion 46 that engages with linkage 44 during use (described below), and two deflectable tabs 48 that can engage with notches or lips (not shown) integrally formed on housing 22 to hold cannula 26 and cannula block 42 in their retracted positions. A compression spring 50 engages cannula block 42 and biases the cannula block distally. Spring 50 can be, e.g., a stainless steel spring having a spring rate of 9.77 lb/in.

Stylet 24 is slidably and coaxially located in cannula 26. Stylet 24 has a distal end 34 configured to penetrate tissue and notch 40 for collecting a tissue sample. Examples of suitable stylet 24 and cannula 26 configurations are exemplified by the ASAP™ Automated Biopsy System having a Delta Cut® needle or a Channel Cut®) needle (available from Boston Scientific Corp., Natick, Mass.), and described in Chu, U.S. Pat. No. 5,989,196, hereby incorporated by reference. From distal end 34, stylet 24 extends into housing 22 where stylet is attached to an axially movable stylet block 52. At its distal portion, stylet block 52 includes a distal post 54 and a distal wall 56, both of which engage with linkage 44 when stylet 24 is moved to its retracted position. At its proximal portion, stylet block 52 includes a proximal wall 58 that is used to hold stylet block 52 in its retracted position, and a proximal post 60. Proximal post 60 can engage with an axially movable lever lock 62, which is used to lock lever 28 in a closed position before stylet 24 and cannula 26 are released to their extended positions. Stylet block 52 further includes two deflectable tabs 64 configured to engage with tabs 48 of cannula block 42 to disengage tabs 48 from housing 22. A compression spring 65 engages stylet block 52 and biases the stylet block distally.

Lever 28 is configured to load cannula 26 and stylet 24 to their retracted positions. Lever 28 is connected to housing 22 by a link 66 having a pin 68, which serves as an axis about which the lever rotates (arrow B). In some embodiments, a torsion spring (not shown) is attached to pin 68 to bias lever 28 toward an open position (FIG. 3A). Lever 28 is connected to a linkage 44 via a pin 45, and a hook 70 (FIG. 2A). A torsion spring (not shown) is attached to pin 45 to bias linkage 44 toward stylet block 52. As described below, during use, linkage 44 engages with cannula block 42 and stylet block 52.

Linkage 44 further includes a curved portion 72 that engages with distal post 54 of stylet block 52. Hook 70 engages with protrusions 74 of lever lock 62 to hold lever 28 in a closed position.

Instrument 20 further includes a mechanism 76 to hold stylet block 52 and to release the stylet block from its retracted position. Mechanism 76 includes a rear latch 78, side trigger 36, and rear trigger 38. Rear latch 78 includes a pin 80 and is mounted in housing 22 such that the rear latch can pivot about the length of the pin (arrow C). Rear latch 78 further includes a hook portion 82, two side members 84 having curved ends 86, and a rear plate 87. Hook portion 82 is configured to engage with, e.g., hook on to, proximal wall 58 of stylet block 52 to hold the stylet block in its retracted position.

Side trigger 36 and rear trigger 38 are configured to move rear latch 78 such that hook portion 82 can disengage from proximal wall 58. Side trigger 36, which is axially slidable (arrow A), includes a side button 85, an end member 88 having a ramped surface 90, and an elongate member 92 connecting the side button and the end member. Ramped surface 90 contacts and engages with curved ends 86 of side members 84. When side button 85 is pulled proximally, end member 88 also moves proximally. As a result, ramped surface 90 engages with curved ends 86 and pivots rear latch 78 such that hook portion 82 can lift and disengage from proximal wall 58. Rear trigger 38 is movably mounted to housing 22 and is configured to engage with rear plate 87. In particular, when depressed, rear trigger 38 pushes against rear plate 87. As a result, rear latch 78 pivots about pin 80, and hook portion 82 can disengage from proximal wall 58.

In some embodiments, instrument 20 also includes a visual indicator that shows when stylet 24 has been loaded to its retracted position. The indicator includes one or more windows 94 formed in housing 22 that allow a user to detect a change in the position of stylet block 52. For example, window(s) 94 can be formed on housing 22 such that tabs 64 of stylet block 52 cover the window(s) when the stylet block is in its extended position. When stylet block 52 is retracted, tabs 64 slide away from window(s) 94 and uncover interior portions of instrument 20. The interior portions can be colored, e.g., red, for enhanced visibility. In other embodiments, window(s) 94 can be aligned with the proximal portion of stylet block 52 having a first color, e.g., green, and the distal portion of the stylet block can have a second color, e.g., red. When stylet block 52 is moved from its extended position to its retracted position, the color visible through window(s) changes from the first color to the second color to indicate that instrument 20 is loaded. Alternatively or in addition, instrument 20 can include window(s) aligned with cannula block 42 to indicate the position of the cannula block. For example, cannula block 42 can be formed with portions with different colors as described above.

FIGS. 3A-3E illustrate a sequence of the operation of instrument 20. Referring to FIG. 3A, instrument 20 is in its rest position, e.g., as taken out of its packaging. Cannula block 42 and stylet block 52 are at their most distal, extended positions. Lever 28 is in its open position, and linkage 44 is adjacent to raised portion 46 of cannula block 42. Lever lock 62 is shown in a distal position.

Figure 3B:
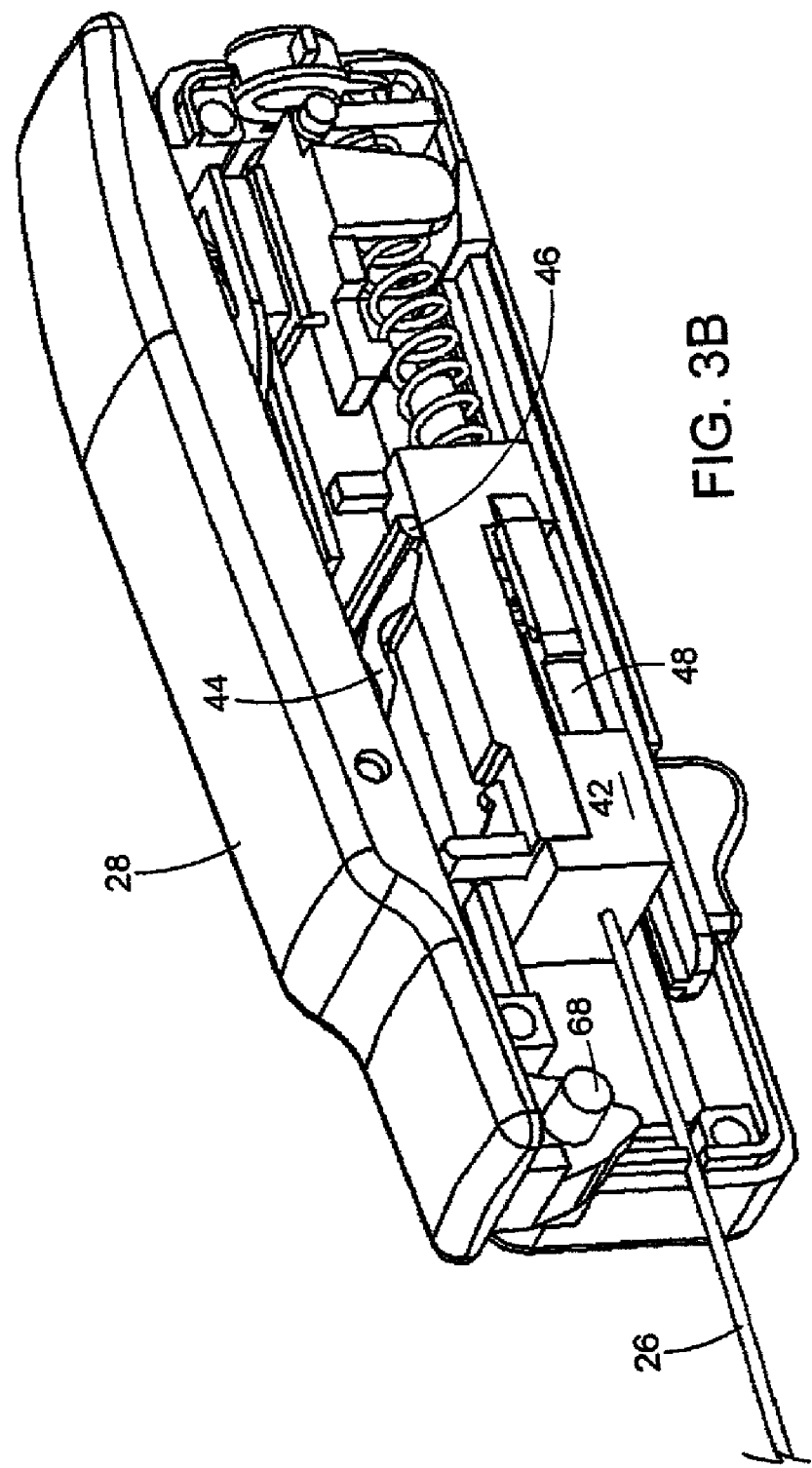

To load or move cannula block 42 and stylet block 52 to their retracted positions, lever 28 is actuated, e.g., closed, two times. Referring to FIG. 3B, when lever 28 is actuated the first time, linkage 44 pivots and engages with raised portion 46 of cannula block 42. As a result, cannula block 42 and cannula 26 are pushed proximally until tabs 48 engage with housing 22, thereby holding the cannula block and the cannula in their retracted positions (FIG. 3B). Cannula block 42 compresses against spring 50. Lever 28 is then released to its open position, e.g., aided by the torsional spring (not shown) attached to pin 68.

Figure 3C:
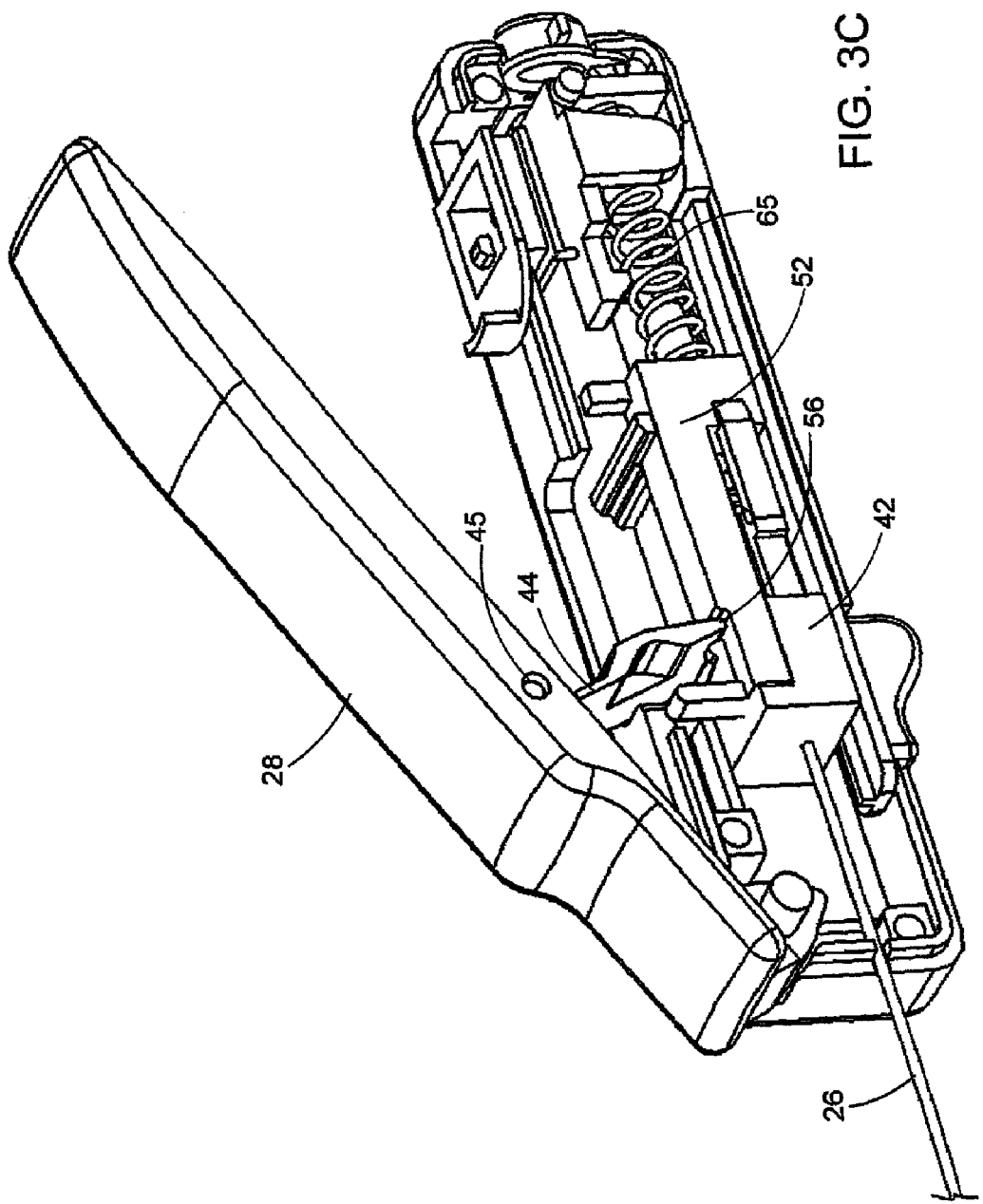
Figure 3D:
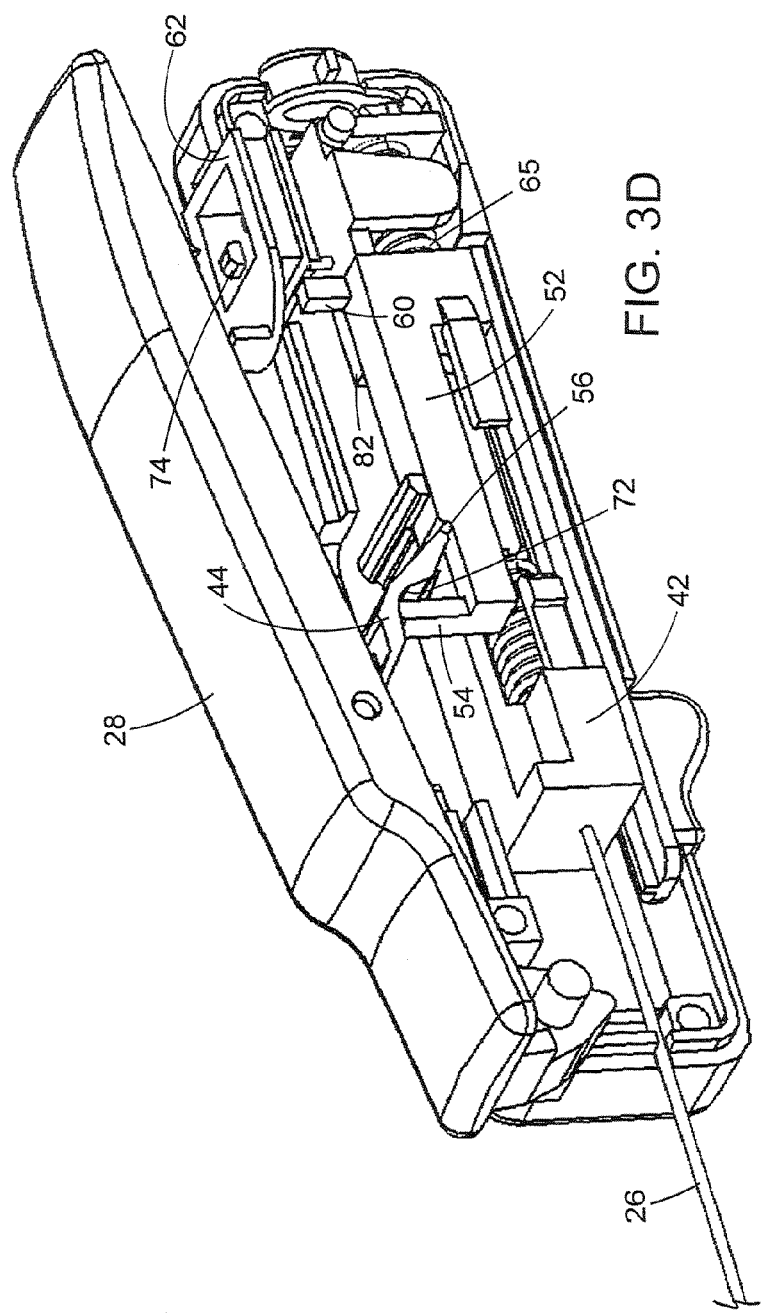
Figure 3E:
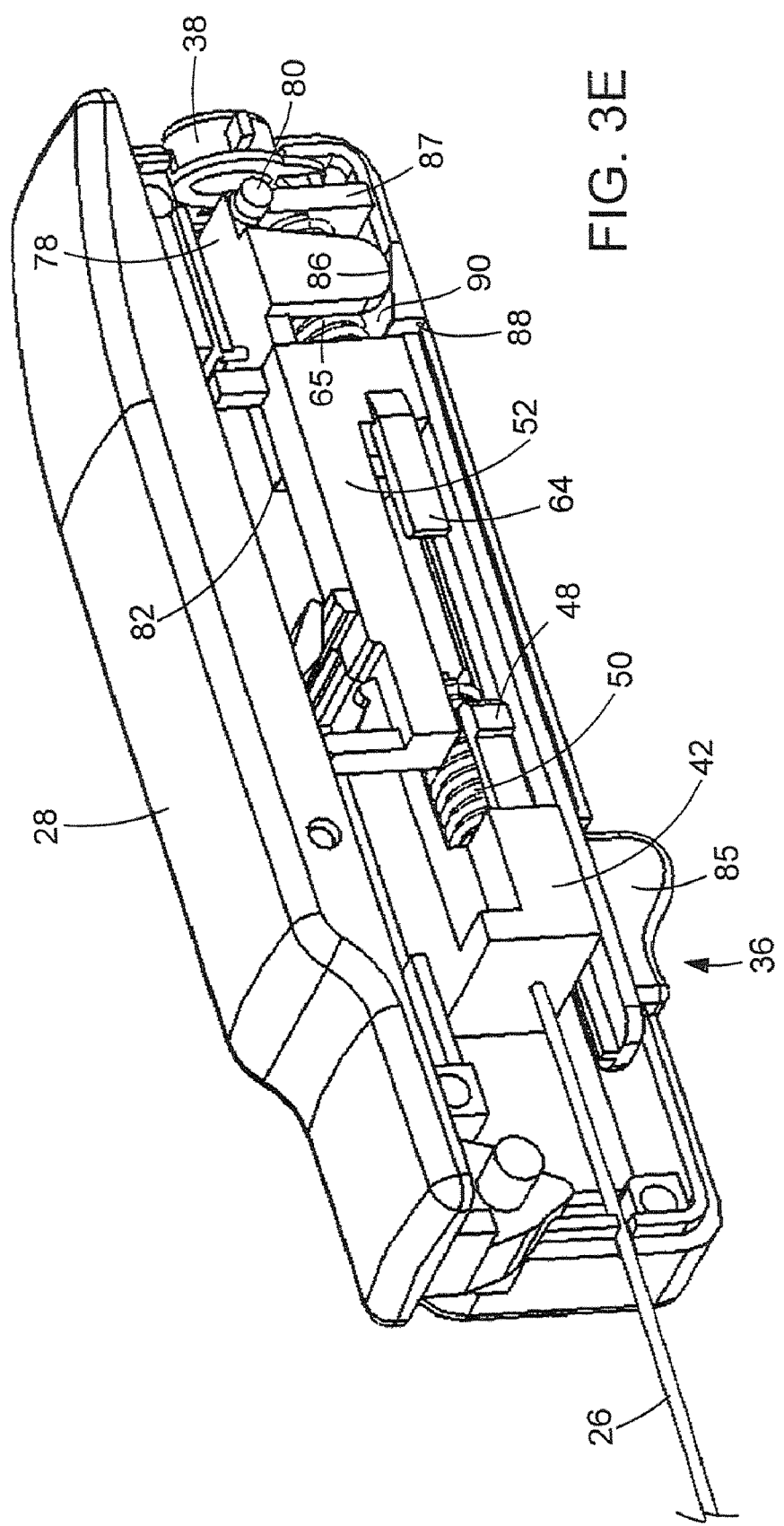

Referring to FIG. 3C, when lever 28 is returned to its open position, linkage 44 engages with distal wall 56 of stylet block 52. The torsion spring (not shown) attached to pin 45 of linkage 44 helps bias the tip of the linkage toward stylet block 52. Lever 28 is then actuated to load stylet block 52 and stylet 24 to their loaded, retracted positions. When lever 28 is actuated, linkage 44 pushes against distal wall 56 and moves stylet block 52 and stylet 24 proximally. Referring to FIG. 3D, as stylet block 52 is pushed further proximally, distal post 54 engages, e.g., contacts, with curved portion 72 of linkage 44. As stylet block 52 is pushed to its retracted position, distal post 54 pushes linkage 44 out of engagement with distal wall 56 and stylet block 52. When stylet block 52 is at its retracted position, hook portion 82 of rear latch 78 engages with proximal wall 58 of the stylet block and holds the stylet block in its retracted position. At the same time, when stylet block 52 is in its retracted position, proximal post 60 pushes lever lock 62 proximally (FIG. 3D). As a result, hook 70 of lever 28 can engage with protrusions 74 of lever lock 62 to hold the lever in a closed position (FIG. 3E). Stylet block 52 compresses against spring 65. Instrument 20 is ready to be triggered or fired.

To fire instrument 20, distal end 34 of stylet 24 is placed adjacent to a target area, and either side trigger 36 or rear trigger 38 can be actuated. To actuate side trigger 36, side button 85 is pulled proximally, e.g., using an index finger, which causes end member 88 to move proximally. As a result, curved ends 86 of side members 84 are advanced over ramped surface 90, which causes rear latch 78 to pivot about pin 80, thereby lifting hook portion 82 out of engagement with proximal wall 58 of stylet block 52. Upon disengagement, stylet block 52 and stylet 24 are propelled distally by the spring force of spring 65, which allows the stylet to penetrate the targeted area. Stylet block 52 then strikes cannula block 42, which disengages tabs 48 of the cannula block from housing 22. In particular, the ramped configuration of the tips of tabs 64 help to wedge tabs 64 between tabs 48 and housing 22 to disengage tabs 48 and cannula block 42 from the housing. Upon disengagement, cannula block 42 and cannula 26 are propelled distally by the spring force of spring 50, which allows the cannula to slide over stylet 24 and to sever a specimen that has prolapsed into notch 40 of the stylet.

Instrument 20 can then be withdrawn. Lever 28 can be returned to its open position by slightly depressing the lever to allow lever lock 62 to move (e.g., distally) and to disengage from hook 70, e.g., similar to the operation of a lockable grip vise. The specimen can be removed from notch 40 by actuating lever 28 once to retract cannula 26. The specimen can be placed on a slide or in a preservative solution. If desired, lever 28 can be actuated to retract and load stylet 24 to collect another specimen.

Rear trigger 38 is actuated by distally pushing the rear trigger, which pushes against rear plate 87. As a result, rear latch 78 pivots about pin 80, and hook portion 82 is lifted out of engagement with proximal wall 58 of stylet block 52. Upon disengagement, stylet 24 and cannula 26 are propelled distally as described above.

Figure 4A:
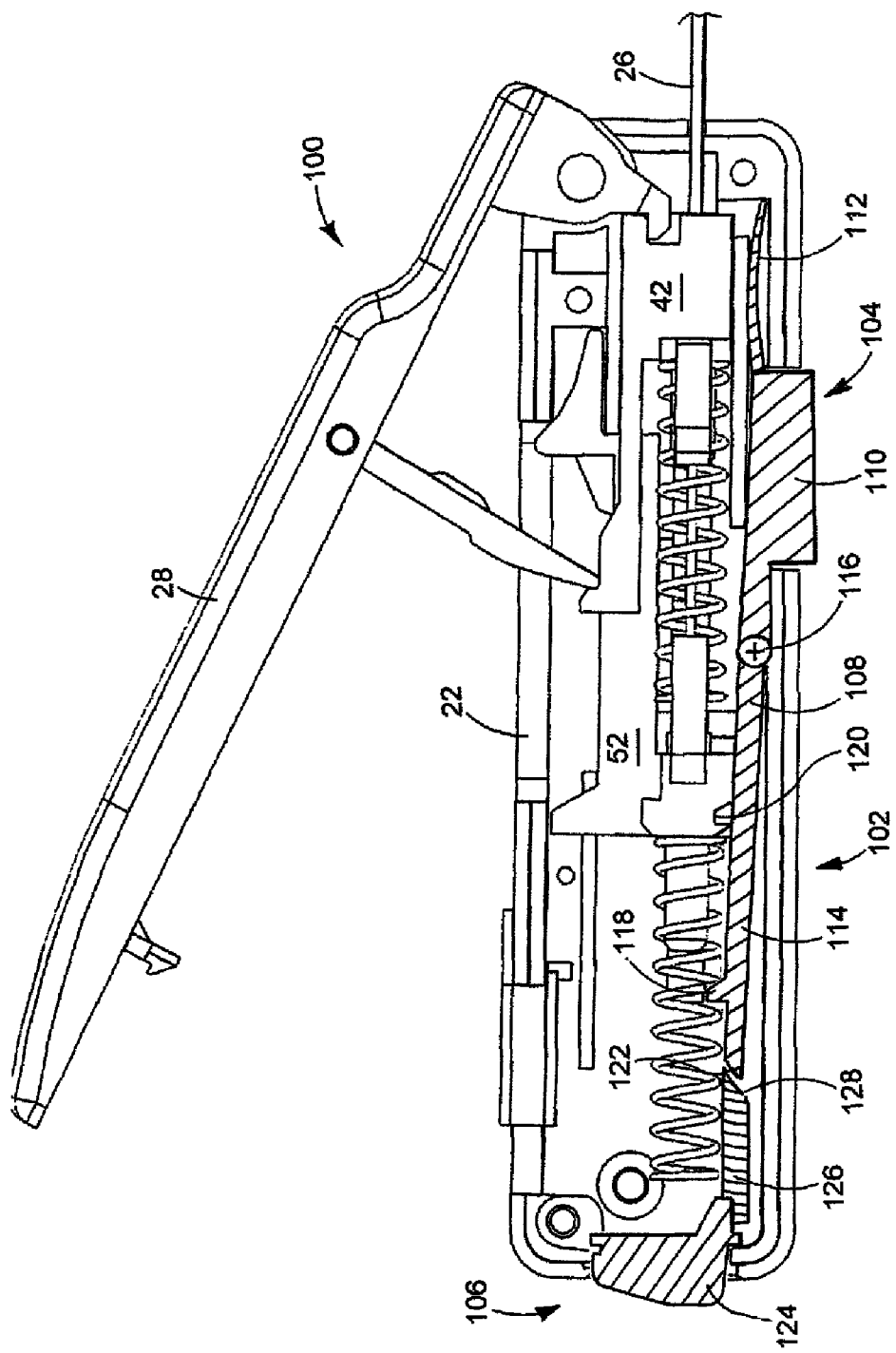
FIG. 4A is a schematic diagram of an embodiment of a biopsy instrument in a rest position.
Figure 4B:
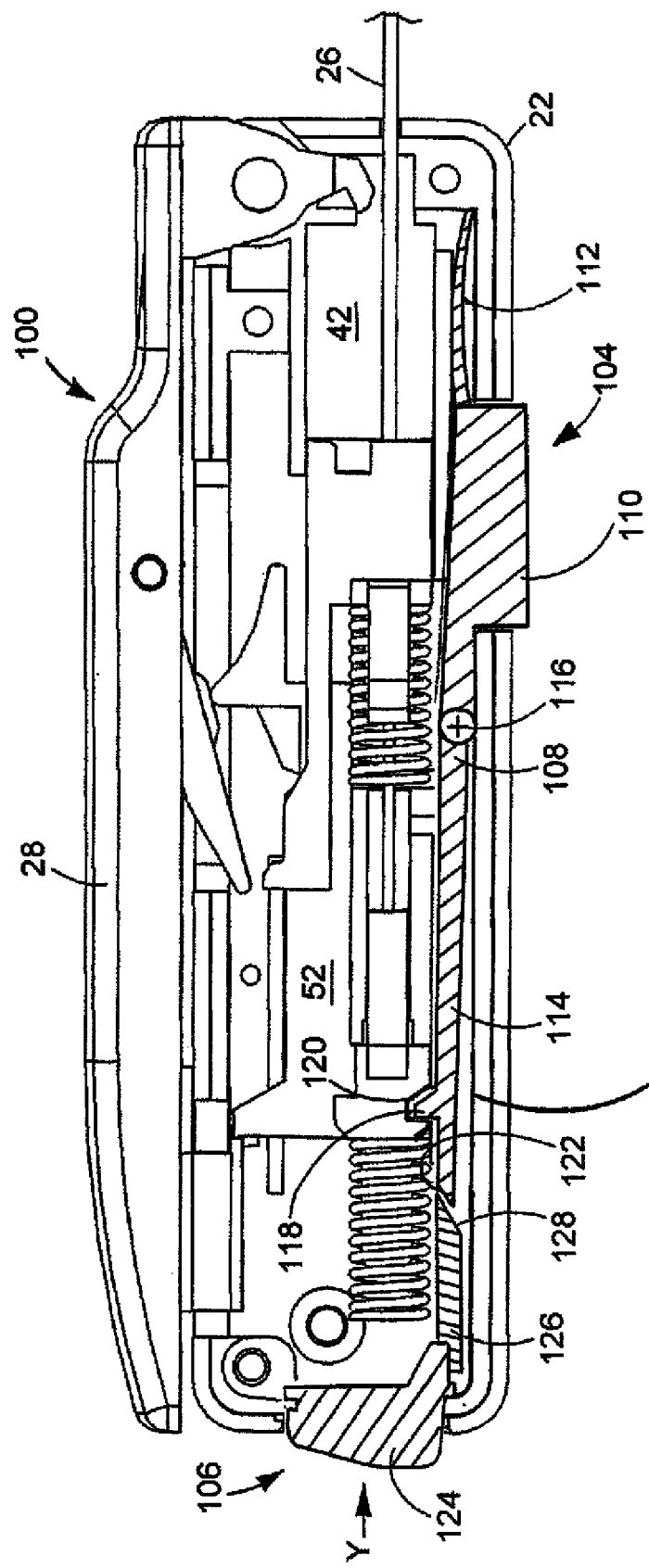
FIG. 4B is a schematic diagram of the instrument of FIG. 4A in a cocked position.

In other embodiments, mechanism 76 used to hold stylet block 52 and to release the stylet block from its retracted position can be modified. Referring to FIGS. 4A and 4B, instrument 100 (generally the same as instrument 20 except as described below) includes a mechanism 102 having a side trigger 104 and a rear trigger 106. Side trigger 104 includes an elongated body 108 having a side button 110, a distal portion 112, and a proximal portion 114. Body 108 is pivotally attached to housing 22 at pivot 116. Distal portion 112 is a generally elongated, curved member that engages portions of housing 22 to bias side button 110 out of the housing (or downward as shown in FIG. 4A). Distal portion 112 also biases proximal portion 114 upward (as shown in FIG. 4A) via pivot 116. Proximal portion 114 includes a projection 118 configured to engage with stylet block 52, specifically, a notch 120 defined by the stylet block. Proximal portion 114 terminates with an angled surface 122. Rear trigger 106 includes a rear button 124 integrally form with a proximal portion 126 that terminates with an angled surface 128. Angled surface 128 contacts angled surface 122, but for clarity, the surfaces are shown spaced from each other.

Operation of instrument 100 is similar to operation of instrument 20. The user retracts cannula block 42 by actuating lever 28 once. When the user actuates lever 28 again, stylet block 52 is moved proximally until projection 118 engages notch 120, thereby holding the stylet block in its retracted position (FIG. 4B). Projection 118 is biased upward (as shown in FIG. 4A) by distal portion 112 and pivot 116 to facilitate engagement with notch 120.

To fire instrument 100, either side trigger 104 or rear trigger 106 can be actuated. To actuate side trigger 104, side button 108 is pushed into housing 22, which overcomes biasing force of distal portion 112 and causes projection 118 to move down (arrow X, as shown in FIG. 4B) via pivot 116. As a result, projection 118 disengages from notch 120, and stylet block 52 and cannula block 42 can be propelled distally as described above.

Rear trigger 106 is actuated by pushing rear button 124 distally (arrow Y). As a result, angled surface 128 contacts, e.g., slides over, angled surface 122, thereby moving proximal portion 114 and projection 118 downward (arrow X) and out of engagement with notch 120. Stylet block 52 and cannula block 42 are propelled distally as described above.

In some embodiments, housing 22 and/or lever 28 can each be made of different materials, e.g., to enhance the grip or "feel" of instrument 20. For example, housing 22 and/or lever 28 can be formed of materials with different hardness, e.g., a core of relatively hard material and an outer layer of relatively soft material. The outer layer can be a foamy material, such as a urethane, to enhance the grip and/or to absorb vibrations from the firing of instrument 20. Each of lever 28 and/or housing 22 can be formed with two or more different materials.

The components of instrument 20 described above can be formed by conventional injection molding techniques, e.g., of polycarbonate and/or ABS. Stylet 24, cannula 26, springs 50 and 65, and the torsion springs can be formed of stainless steel.

Terms, such as "left", "right", and "rear", are used to describe the embodiment as shown in the orientation of the figures, and not intended to be limiting.

Other embodiments are within the claims.

What is claimed is:

1. A medical instrument comprising:
   a housing;
   a stylet having a portion in the housing and extending through a first end of the housing, the stylet being movable between an extended position and a refracted position;
   a stylet block attached to the stylet;
   a cannula coaxially receiving the stylet, the cannula having a portion in the housing, and extending through the first end of the housing, the cannula being movable between an extended position and a retracted position;
   a cannula block attached to the cannula;
   a lever connected to the housing such that the lever rotates about an axis at the first end of the housing; and
   a link member comprising a first end and a second end located opposite of the first end, the first end of the link member pivotably attached to the lever and the second end of the link member free to rotate about the first end of the link member;
   wherein the second end of the link member is operable to engage the cannula block when the cannula is in the extended position of the cannula and is operable to engage the stylet block when the cannula is in the retracted position of the cannula.

2. The medical instrument of claim 1, further comprising a first resilient member biasing the lever towards an open position.

3. The medical instrument of claim 2, further comprising a lever lock operable to hold the lever in a closed position.

4. The medical instrument of claim 2, further comprising a second resilient member biasing the link member towards the cannula.

5. The medical instrument of claim 1, wherein a first part of the stylet block comprises a protrusion extending towards the link member, the protrusion operable to contact the link member when the stylet is in the retracted position of the stylet such that the link member disengages from a second part of the stylet block different from the first part of the stylet block comprising the protrusion.

6. The instrument of claim 1, further comprising a latch in the housing, the latch and the stylet block engaging when the stylet is in the retracted position.

7. The instrument of claim 6, further comprising a first trigger engageable with the latch to release the stylet from the retracted position.

8. The instrument of claim 6, wherein the first trigger pivotally moves the latch to disengage the latch from the stylet block.

9. The instrument of claim 1, further comprising a second trigger engageable with the latch to release the stylet from the retracted position.

10. A medical instrument, comprising:
    a housing;
    a stylet having a portion in the housing and extending through a first end of the housing, the stylet being movable between an extended position and a refracted position;
    a cannula coaxially receiving the stylet, the cannula having a portion in the housing and extending through the first end of the housing, the cannula being movable between an extended position and a retracted position;
    a lever connected to the housing such that the lever rotates about an axis at the first end of the housing; and
    a link member comprising a first end and a second end located opposite of the first end, the first end of the link member pivotably attached to the lever and the second end of the link member free to rotate about the first end of the link member;
    wherein the second end of the link member is operable to apply force to the cannula when the cannula is in the extended position of the cannula and is operable to apply force to the stylet when the cannula is in the retracted position of the cannula.

11. The medical instrument of claim 10, further comprising a first resilient member biasing the lever towards an open position.

12. The medical instrument of claim 10, further comprising a second resilient member biasing the link member towards the cannula.

13. The medical instrument of claim 10, wherein a first part of the stylet block comprises a protrusion extending towards the link member, the protrusion operable to contact the link member when the stylet is in the retracted position of the stylet such that the link member disengages from a second part of the stylet block different from the first part of the stylet block comprising the protrusion.

14. The instrument of claim 10, further comprising:
a stylet block attached to a proximal end of the stylet; and
a cannula block attached to a proximal end of the cannula;
wherein the second end of the link member is operable to engage the cannula block when the cannula is in the extended position of the cannula and is operable to engage the stylet block when the cannula is in the retracted position of the cannula.

15. The instrument of claim 10, further comprising a first trigger configured to release the stylet from the retracted position, the first trigger and the lever located on opposing surfaces of the housing.

16. The instrument of claim 15, further comprising a second trigger configured to release the stylet from the retracted position.

17. A medical instrument, comprising:
a housing;
a stylet having a portion in the housing and extending through a first end of the housing, the stylet being movable between an extended position and a refracted position;
a cannula coaxially receiving the stylet, the cannula having a portion in the housing and extending through the first end of the housing, the cannula being movable between an extended position and a retracted position;
a lever connected to the housing by a link with a pin such that the lever rotates about an axis at the first end of the housing; and
a first resilient member biasing the link towards the cannula,
wherein the medical instrument is configured such that the lever is capable of sequentially moving the cannula from the extended position of the cannula to the retracted position of the cannula and moving the stylet from the extended position of the stylet to the retracted position of the stylet.

18. The medical instrument of claim 17, further comprising a link member comprising a first end and a second end located opposite of the first end, the first end of the link member pivotably attached to the lever and the second end of the link member free to rotate about the first end of the link member;
wherein the second end of the link member is operable to engage the cannula block when the cannula is in the extended position of the cannula and is operable to engage the stylet block when the cannula is in the retracted position of the cannula.

19. The medical instrument of claim 17, wherein a first part of the stylet block comprises a protrusion extending towards the link member, the protrusion operable to contact the link member when the stylet is in the retracted position of the stylet such that the link member disengages from a second part of the stylet block different from the first part of the stylet block comprising the protrusion.

* * * * *

UNITED STATES PATENT AND TRADEMARK OFFICE
CERTIFICATE OF CORRECTION

| | | |
|---|---|---|
| PATENT NO. | : 8,043,228 B2 | Page 1 of 1 |
| APPLICATION NO. | : 12/498206 | |
| DATED | : October 25, 2011 | |
| INVENTOR(S) | : David Cooke | |

It is certified that error appears in the above-identified patent and that said Letters Patent is hereby corrected as shown below:

IN THE CLAIMS:

Column 7, Claim 1, Line 63: delete "refracted" and insert --retracted--.

Column 8, Claim 10, Line 47: delete "refracted" and insert --retracted--.

Column 9, Claim 17, Line 30: delete "refracted" and insert --retracted--.

Signed and Sealed this
Twentieth Day of December, 2011

David J. Kappos
*Director of the United States Patent and Trademark Office*